United States Patent
Seidel et al.

(10) Patent No.: US 7,176,226 B2
(45) Date of Patent: Feb. 13, 2007

(54) CRYSTAL MODIFICATION II OF 2-[2-(1-CHLORO-CYCLOPROPYL)-3-(2-CHLOROPHENYL)-2-HYDROXY-PROPYL]-2,4-DIHYDRO-3H-1,2,4-TRIAZOLE-3-THIONE

(75) Inventors: Erika Seidel, Königswinter (DE); Ronald Vermeer, Leverkusen (DE); Karin Hasenack, Schwelm (DE); Britta Olenik, Bottrop (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 10/521,715

(22) PCT Filed: Jul. 10, 2003

(86) PCT No.: PCT/EP03/07473

§ 371 (c)(1),
(2), (4) Date: Nov. 7, 2005

(87) PCT Pub. No.: WO2004/008860

PCT Pub. Date: Jan. 29, 2004

(65) Prior Publication Data

US 2006/0106080 A1    May 18, 2006

(30) Foreign Application Priority Data

Jul. 22, 2002 (DE) .................. 102 33 171

(51) Int. Cl.
*A01N 43/653* (2006.01)
*C07D 249/12* (2006.01)

(52) U.S. Cl. .................... 514/384; 548/263.2
(58) Field of Classification Search ........... 514/384; 548/263.2
See application file for complete search history.

(56) References Cited

U.S. PATENT DOCUMENTS 5,789,430 A * 8/1998 Jautelat et al. .............. 514/384

FOREIGN PATENT DOCUMENTS

WO        96/16048        5/1996

OTHER PUBLICATIONS

Angew. Chem. Int. Ed. 38, (month unavailable) 1999, pp. 3440-3461, Joel Bernstein et al, "Concomitant Polymorphs".
J. Pharm. Sci., vol. 58, Aug. 1969, pp. 911-929, John Haleblian et al, "Pharmaceutical Applications of Polymorphism".

* cited by examiner

*Primary Examiner*—Kamal A. Saeed
(74) *Attorney, Agent, or Firm*—Richard E. L. Henderson

(57) ABSTRACT

This invention relates to crystal form II of 2-[2-(1-chloro-cyclopropyl)-3-(2-chloropenyl)-2-hydroxypropyl]-2,4-dihydro-3H-1,2,4-triazole-3-thione of the formula (A)

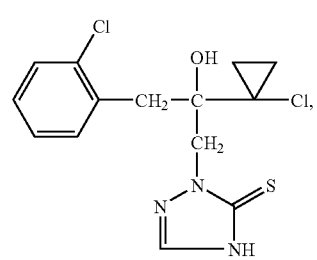

to a process for its preparation and to its use for controlling unwanted microorganisms.

5 Claims, 4 Drawing Sheets

CRYSTAL MODIFICATION II OF 2-[2-(1-CHLORO-CYCLOPROPYL)-3-(2-CHLOROPHENYL)-2-HYDROXY-PROPYL]-2,4-DIHYDRO-3H-1,2,4-TRIAZOLE-3-THIONE

RELATED APPLICATIONS

The present patent application has been filed under 35 U.S.C. 371 as a national stage application of PCT/EP2003/007473, filed Jul. 10, 2003, which was published in German as International Patent Publication WO 2004/008860 on Jan. 29, 2004, which is entitled to the right of priority of German Patent Application 102 33 171.5, filed Jul. 22, 2002.

BACKGROUND OF THE INVENTION

The present invention relates to the crystal form II of 2-[2-(1-chlorocyclopropyl)-3-(2-chlorophenyl)-2-hydroxypropyl]-2,4-dihydro-3H-1,2,4-triazole-3-thione, to a process for preparing this substance and to its use for controlling unwanted midroorganisms.

2-[2-(1-Chlorocyclopropyl)-3-(2-chlorophenyl)-2-hydroxypropyl]-2,4-dihydro-3H-1,2,4-triazole-3-thione and its use as microbicide, in particular as fungicide, are already known (cf. WO 96-16 048). It is also known that this substance can be prepared by reacting 2-(1-chlorocyclopropyl)-1-(2-chlorophenyl)-3-(1,2,4-triazol-1-yl)propan-2-ol either (a) with sulphur in the presence of N-methylpyrrolidone at temperatures of about 200° C. or (b) initially with n-butyllithium in the presence of hexane and then with sulphur in the presence of tetrahydrofuran (cf. WO 96-16 048). It has now been found that the active compound can be obtained in two different crystal forms, of which form I is metastable at room temperature and form II is thermodynamically stable at room temperature.

If active compounds occur in different crystal forms (=polymorphism), this is of great importance both for designing preparation processes and for developing formulations. Thus, the different forms of a chemical compound differ, in addition to appearance (crystal habit) and hardeness, also in numerous further physicochemical properties. Here, differences in stability, solubility, hygroscopicity, melting point, particle density and flowability may exert a strong influence on the quality and the effectiveness of crop treatment agents. Hitherto, it has not been possible to predict the occurrence and the number of crystal forms including their physicochemical properties. In particular, the thermodynamic stability and also the different behaviour following administration to living organisms cannot be determined a priori.

It is generally known that the different forms of a substance can be monotropic or enantiotropic. In the case of monotropic polymorphism, a crystal form may represent the thermodynamically stable phase over the entire temperature range up to the melting point, whereas in the case of enantiotropic systems there is a transition point in which the stability relation is reversed. It is not possible to predict the stability relation, in particular the existence and the position of such a transition point. An up-to-date review of the prior art with respect to these principal thermodynamic relations is given in Angew. Chem. Int. Ed. 1999, 38, 3440–3461.

SUMMARY OF THE INVENTION

We have now found the crystal form II of 2-[2-(1-chlorocyclopropyl)-3-(2-chlorophenyl)-2-hydroxypropyl]-2,4-dihydro-3H-1,2,4-triazole-3-thione of the formula

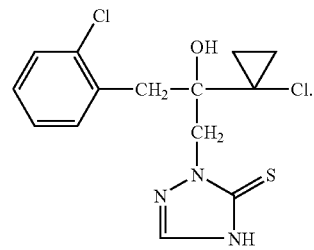

(A)

Furthermore, we have found that the crystal form II of 2-[2-(1-chlorocyclopropyl)-3-(2-chlorophenyl)-2-hydroxypropyl]-2,4-dihydro-3H-1,2,4-triazole-3-thione of the formula (A) can be prepared by treating the crystal form I of this substance in the presence of water and/or one or more aliphatic alcohols having 1 to 10 carbon atoms and/or one or more dialkyl ketones having 1 to 4 carbon atoms in each alkyl moiety and/or one or more alkyl alkylcarboxylates having 1 to 4 carbon atoms in each alkyl moiety at temperatures between 0° C. and 90° C.

Finally, it has been found that the crystal form II of 2-[2-(1-chlorocyclopropyl)-3-(2-chlorophenyl)-2-hydroxypropyl]-2,4-dihydro-3H-1,2,4-triazole-3-thione of the formula (A) is highly suitable for controlling unwanted microorganisms, in particular fungi.

DETAILED DESCRIPTION OF THE INVENTION

Compared to the corresponding thermodynamically stable forms, metastable crystal forms generally have disadvantages. Thus, a metastable form may adversely affect the preparation process and the stability of the active compound or its formulations during transport or on storage. From J. Pharm. Sci. 1969, 58, 911, for example, it is known that, when a thermodynamically metastable crystal form is used, partial or complete conversion into another polymorphic form may take place during preparation or on storage. This leads to unwanted crystal growth (recrystallizations), changes in bioavailability, caking or agglomeration, the transformation being spontaneous or taking place over a relatively long period of time and not being predictable.

The metastable form I of 2-[2-(1-chlorocyclopropyl)-3-(2-chlorophenyl)-2-hydroxypropyl]-2,4-dihydro-3H-1,2,4-triazole-3-thione, too, has physicochemical properties which are unfavourable for use in practice. In contrast, the form II according to the invention is thermodynamically stable, and neither its preparation nor its storage, neat or in the form of formulations, in particular suspension concentrates, causes any problems. The existence of the crystal form II according to the invention of the triazole derivative of the formula (A) is unexpected, since its occurrence could not have been predicted based on the prior art.

At a pressure of 1013 mbar, the crystal form II according to the invention of the triaxole derivative of the formula (A) is stable below 90° C. It has a melting point of 138° C. and can be characterized by Raman spectroscopy.

Figure 1:
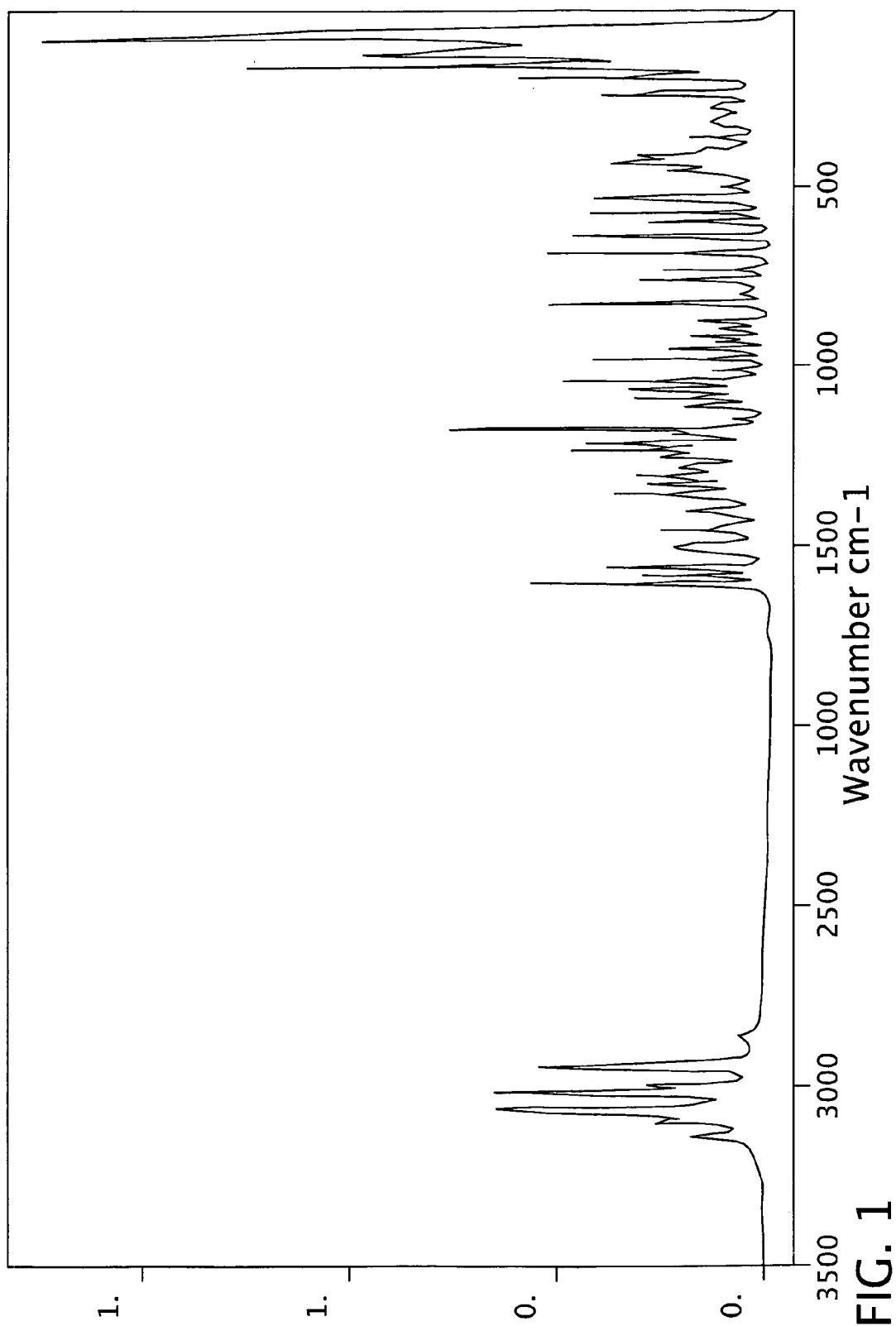
FIG. 1 shows a Raman spectrum of the crystal form II of the triazole derivative of the formula (A).

FIG. 1 shows a Raman spectrum of the crystal form II of the triazole derivative of the formula (A). The values of the peak maxima are listed in Table 1 below.

TABLE 1

Wave numbers of the bands in Raman spectra of crystal form II of the triazole derivative of the formula (A)

| Wave numbers [cm$^{-1}$] |
| --- |
| 3220 |
| 3151 |
| 3063 |
| 3016 |
| 2927 |
| 1542 |
| 1476 |
| 1455 |
| 1445 |
| 1424 |
| 1407 |
| 1375 |
| 1351 |
| 1339 |
| 1324 |
| 1290 |
| 1220 |
| 1204 |
| 1184 |
| 1169 |
| 1137 |
| 1123 |
| 1101 |
| 1065 |
| 1052 |
| 1038 |
| 1032 |
| 1001 |
| 963 |
| 954 |
| 922 |
| 912 |
| 889 |
| 876 |
| 869 |
| 849 |
| 822 |
| 796 |
| 782 |
| 759 |
| 752 |
| 748 |
| 725 |
| 680 |

Figure 2:
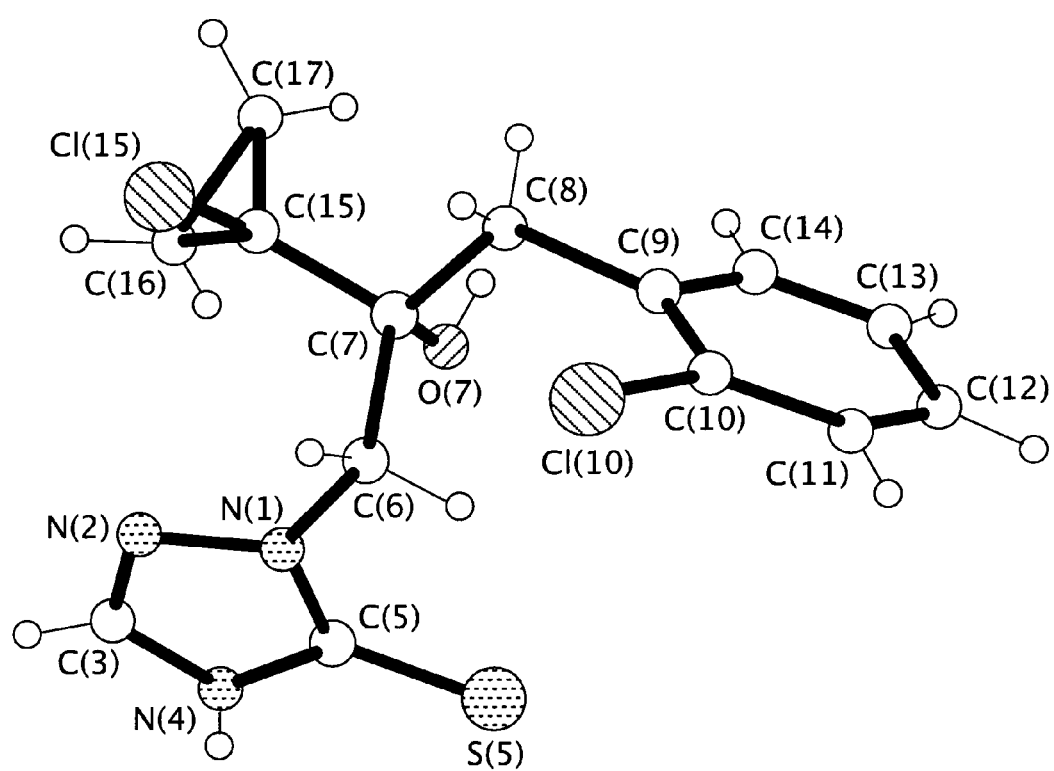
FIGS. 2 and 3 show representations of the crystal structure of crystal form II of the triazole derivative of the formula (A) as determined by single crystal X-ray structural analysis.

FIG. 2 shows the crystal structure of crystal form II of the triazole derivative of the formula (A), determined by single crystal X-ray structural analysis. The most important parameters, which characterize the crystal structure unambiguously, are listed in Table 2 below.

TABLE 2

Bond lengths and angles in crystals of crystal form II of the triazole derivative of the formula (A)

| Bond | Length [Å] | Bonds | Angle [°] |
| --- | --- | --- | --- |
| N(1)-C(5) | 1.350 (3) | C(5)-N(1)-N(2) | 112.8 (2) |
| N(1)-C(6) | 1.454 (3) | N(2)-N(1)-C(6) | 120.6 (2) |
| C(3)-N(4) | 1.360 (3) | N(2)-C(3)-N(4) | 111.9 (2) |
| S(5)-C(5) | 1.689 (2) | N(1)-C(5)-N(4) | 103.6 (2) |
| O(7)-C(7) | 1.433 (3) | N(4)-C(5)-S(5) | 127.8 (2) |
| C(7)-C(8) | 1.539 (3) | O(7)-C(7)-C(6) | 104.8 (2) |
| C(9)-C(14) | 1.393 (4) | C(6)-C(7)-C(15) | 113.6 (2) |
| Cl(10)-C(10) | 1.743 (3) | C(6)-C(7)-C(8) | 109.9 (2) |
| C(11)-C(12) | 1.384 (4) | C(9)-C(8)-C(7) | 117.2 (2) |
| C(13)-C(14) | 1.391 (4) | C(14)-C(9)-C(8) | 119.6 (2) |
| C(15)-C(16) | 1.490 (4) | C(11)-C(10)-C(9) | 122.4 (2) |
| C(16)-C(17) | 1.521 (4) | C(9)-C(10)-Cl(10) | 120.1 (3) |
| N(1)-N(2) | 1.377 (3) | C(13)-C(12)-C(11) | 119.9 (3) |
| N(2)-C(3) | 1.301 (4) | C(13)-C(14)-C(9) | 121.9 (3) |
| N(4)-C(5) | 1.361 (3) | C(16)-C(15)-C(7) | 123.2 (2) |
| C(6)-C(7) | 1.533 (3) | C(16)-C(15)-Cl(15) | 115.7 (2) |
| C(7)-C(15) | 1.536 (3) | C(7)-C(15)-Cl(15) | 112.2 (2) |
| C(8)-C(9) | 1.515 (3) | C(15)-C(17)-C(16) | 59.0 (2) |
| C(9)-C(10) | 1.395 (4) | C(5)-N(1)-C(6) | 126.6 (2) |
| C(10)-C(11) | 1.382 (4) | C(3)-N(2)-N(1) | 103.5 (2) |
| C(12)-C(13) | 1.379 (5) | C(3)-N(4)-C(5) | 108.2 (2) |
| Cl(15)-C(15) | 1.773 (3) | N(1)-C(5)-S(5) | 128.5 (2) |
| C(15)-C(17) | 1.503 (4) | N(1)-C(6)-C(7) | 113.3 (2) |
|  |  | O(7)-C(7)-C(15) | 108.9 (2) |
|  |  | O(7)-C(7)-C(8) | 111.7 (2) |
|  |  | C(15)-C(7)-C(8) | 108.1 (2) |
|  |  | C(14)-C(9)-C(10) | 116.5 (2) |
|  |  | C(10)-C(9)-C(8) | 123.9 (2) |
|  |  | C(11)-C(10)-Cl(10) | 117.4 (2) |
|  |  | C(10)-C(11)-C(12) | 119.5 (3) |
|  |  | C(12)-C(13)-C(14) | 119.8 (3) |
|  |  | C(16)-C(15)-C(17) | 61.1 (2) |
|  |  | C(17)-C(15)-C(7) | 120.6 (2) |
|  |  | C(17)-C(15)-Cl(15) | 115.1 (2) |
|  |  | C(15)-C(16)-C(17) | 59.9 (2) |

Figure 3:
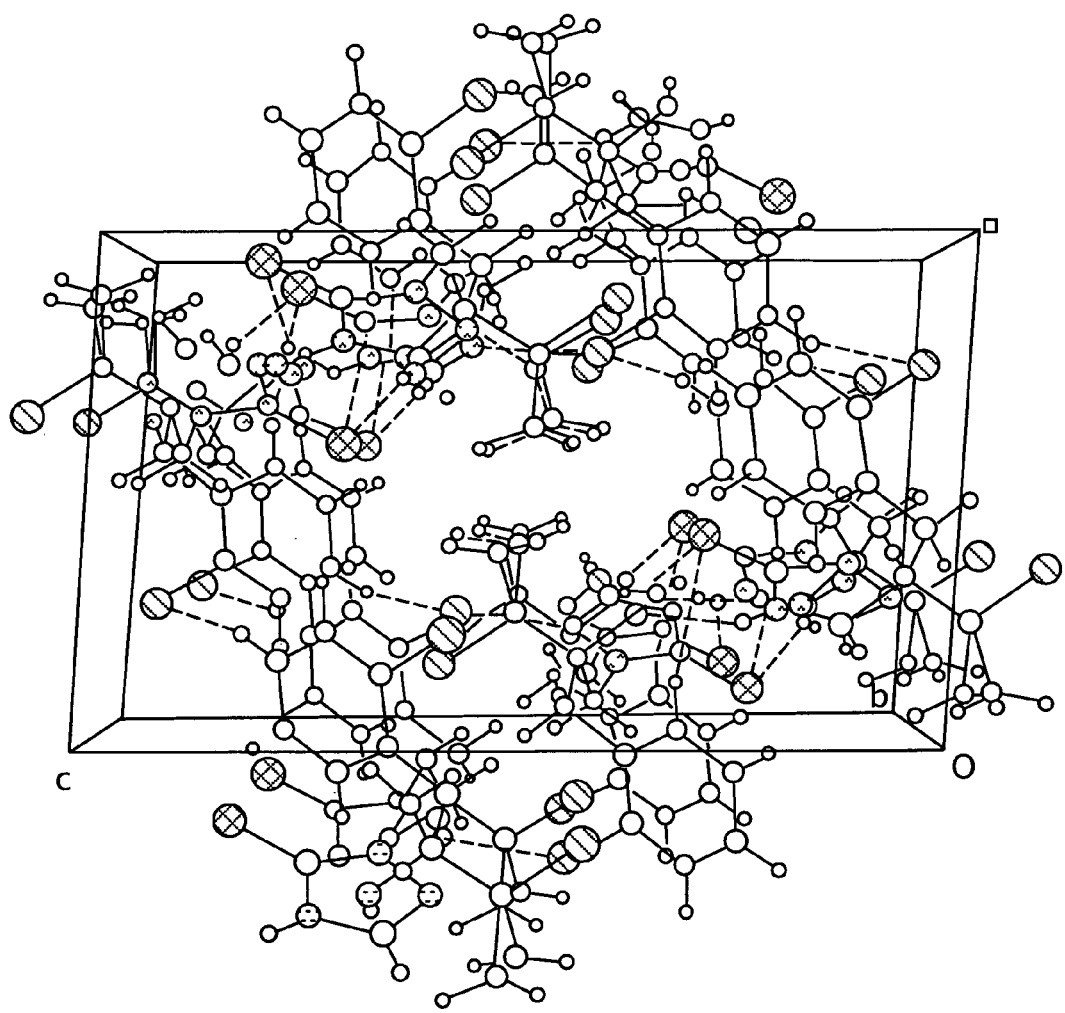

FIG. 3 shows the crystal structure of crystal form II of the triazole derivative of the formula (A), determined by single crystal X-ray structural analysis. The most important parameters, which characterize the crystal structure unambiguously, are listed in Table 3 below.

TABLE 3

Crystallographic data of crystal form II of the triazole derivative of the formula (A) (crystal structure)

| | | |
| --- | --- | --- |
| Symmetry class | monocline | |
| Space group | P2$_1$/n | |
| Dimensions | a = 9.8927(8) Å | α = 90° |
| | b = 9.5635 (8) Å | β = 92.651 (6)° |
| | c = 16.4448 (10) Å | γ = 90° |
| Volume | 1554.2 (2) Å$^3$ | |
| Z coordinate | 4 | |
| Density (calculated) | 1.471 Mg/m$^3$ | |

The crystal form I of the triazole derivative of the formula (A) required as starting material for preparing the substance according to the invention is known (cf. WO 96-16 048). It has a melting point of 140.3° C. and can be characterized by Raman spectroscopy.

Figure 4:
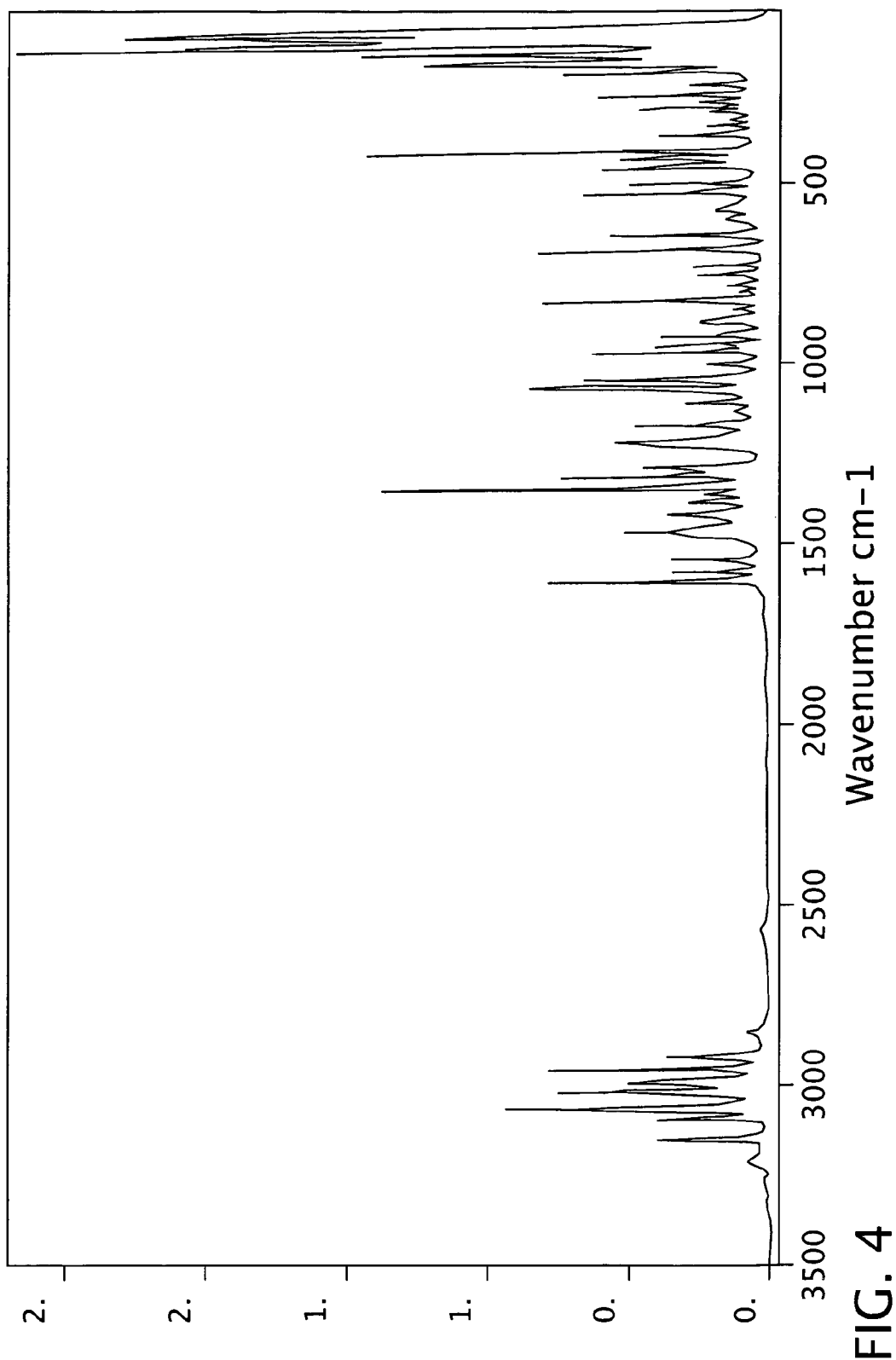
FIG. 4 shows a Raman spectrum of crystal form I of the triazole derivative of the formula (A).

FIG. 4 shows a Raman spectrum of crystal form I of the triazole derivative of the formula (A). The values of the peak maxima are listed in Table 4 below.

TABLE 4

Wave numbers of the bands in Raman spectra of crystal form I of the triazole derivative of the formula (A)

| Wave numbers [cm$^{-1}$] |
|---|
| 3312 |
| 3134 |
| 3070 |
| 3014 |
| 2936 |
| 1559 |
| 1488 |
| 1475 |
| 1437 |
| 1424 |
| 1406 |
| 1388 |
| 1346 |
| 1341 |
| 1291 |
| 1270 |
| 1218 |
| 1172 |
| 1133 |
| 1094 |
| 1066 |
| 1061 |
| 1053 |
| 1036 |
| 1032 |
| 1001 |
| 972 |
| 947 |
| 913 |
| 868 |
| 818 |
| 779 |
| 755 |
| 748 |
| 728 |
| 678 |

The particle densities of crystal forms I and II of the triazole derivative of the formula (A) are compared in Table 5 below.

TABLE 5

Particle densities of crystal forms

| Polymorph | Density [Mg/m$^3$] |
|---|---|
| (form I), experimental | 1.39 |
| (form I), calculated from SCA | 1.432 |
| (form II), experimental | 1.43 |
| (form II), calculated from SCA | 1.471 |

A DSC Pyris 1 from Perkin Elmer was used to determine the melting points. The measurements were carried out using a heating rate of 10 K min$^{-1}$. In each case, the given melting points refer to the peak maximum under the given conditions. The Raman spectra of the crystal forms were recorded using an RFS 100/S FT-Raman from Bruker (128 scans per measurement). The particle density was determined experimentally according to method SOP 5024 for determining densities using the Ultrapyknometer 1000 T from Quanta-Chrome or theoretically from the single crystal. X-ray structural analysis (SCA). The single crystal X-ray structural analysis was carried out using a P4RA four-cycle diffractometer from Siemens with rotating anode generator, graphite monochromator, scintillation counter and low-temperature unit. Measurement was carried out using molybdenum radiation of a wavelength of 0.71073 (MoK$_\alpha$).

The measurement data given above indicate that crystal forms I and II of the triazole derivative of the formula (A) can be characterized unambiguously by the melting point, which is clearly different, and additionally also by the respective Raman spectrum and by the particle density.

Preferred diluents for carrying out the process according to the invention are water, methanol, ethanol, 2-propanol, acetone, 2-butanone and ethyl acetate. Here, the solvents can be used both individually and in the form of mixtures.

When carrying out the process according to the invention, the temperatures can be varied within a certain range. In general, the process is carried out at temperatures between 0° C. and 90° C., preferably at temperatures between 0° C. and 80° C., particularly preferably between 50° C. and 80° C.

The process according to the invention is generally carried out under atmospheric pressure. However, it is also possible to operate under elevated pressure.

When carrying out the process according to the invention, in general the respectively desired amount of crystal form I of the triazole derivative of the formula (A) is suspended or dissolved in the diluent in question, and the mixture is then stirred at the particular temperature desired until conversion into crystal form II has taken place. Here, the reaction time depends both on the reaction temperature and on the diluent. Moreover, the conversion rate depends on whether seed crystals of crystal form II ate present. At higher temperatures, the conversion proceeds more rapidly than at low temperatures. If a solvent is used in which crystal form I of the triazole derivative of the formula (A) is completely soluble, the conversion into crystal form II proceeds more rapidly than in the case where suspensions are used in which the starting material is only slightly soluble, if at all. Also, conversion of crystal form I into crystal form II is accelerated by the presence of seed crystals of crystal form II.

In general, conversion of crystals of form I into form II can be achieved directly at elevated temperature by crystallization with cooling to room temperature, without the use of seed crystals. Without the use of seed crystals, the conversion of a suspension of crystals of form I into form II requires a period of 7 to 14 days. In contrast, if seed crystals of form II are added during conversion of a suspension of crystals of form I into form II, a treatment time of 24 to 48 hours is generally sufficient to achieve quantitative conversion into crystal form II. In each case, it is possible to extend the duration of the treatment without crystal form I being reformed.

The isolation of the crystals of form II is in each case carried out by customary methods. If a suspension is present, the crystals of form II are generally filtered off and dried.

If, in the practice of the process according to the invention, the conversion into crystal form II is not quantitative, a mixture of crystals of forms I and II is obtained. However, since crystal form I is thermodynamically less stable than form II, the active compound according to the invention should only contain a small proportion of crystal form I. The products according to the invention generally comprise less than 10% by weight of crystal form I, preferably less than 5% by weight and particularly preferably less than 2% by weight of crystal form I.

Owing to its thermodynamic stability, the crystal form II according to the invention of the triazole derivative of the formula (A) is highly suitable for preparing formulations, even if, following preparation of the formulation, the active compound is no longer present in crystalline form but in solution. It is particularly advantageous that the crystal form II of the triazole derivative of the formula (A) is in each case converted quantitatively into the desired formulation. This decisively reduces the risk of inaccurate dosage owing to agglomerization and/or sedimentation.

The active compound according to the invention, i.e. the triazole derivative of the formula (A) in crystal form II, has excellent microbicidal action and can be employed for controlling unwanted microorganisms, such as fungi and bacteria, in crop protection and in the protection of materials.

The active compound according to the invention can be used to treat plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

Treatment of the plants and parts of plants with the active compound according to the invention is carried out directly or by action on their surroundings, habitat or storage space by the customary treatment methods, for example by immersion, spraying, evaporating, fogging, scattering, painting on and, in the case of propagation material, in particular in the case of seeds, also by applying one or more coats.

In the protection of materials, the compound according to the invention can be employed for protecting industrial materials against infection with, and destruction by, unwanted microorganisms.

The crystal form of the triazole derivative of the formula (A) can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compound with extenders, that is liquid solvents, liquefied gases under pressure, and/or solid carriers, optionally with the use of surfactants, that is emulsifiers and/or dispersants and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformanide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compound according to the invention can be used as such or in its formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following compounds:

Fungicides:

aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, carpropamid, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenhexamid, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, fluoxastrobin, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, iprovalicarb, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCNB), quinoxyfen sulphur and sulphur preparations, spiroxamine tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-metyl-1H-1,2,4-triazole-1-ethanol,

α-(5-methyl-1,3-dioxan-5-yl)-β-[[4-(trifluoromethyl)phenyl]methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyiino)-N-methyl-2-phenoxyphenylacetamide, 1-(2,4-dichlorophenyl)-2-(1H-1,2,4-triazol-1-yl)ethanone O-(phenylmethyl)oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)sulphonyl]-4-methylbenzene, 1-[[2-(2,4-dichlorophenyl)-1,3-dioxolan-2-yl]methyl]-1H-imidazole, 1-[[2-(4-chlorophenyl)-3-phenyloxiranyl]methyl]-1H-1,2,4-triazole, 1-[1-[2-[(2,4-dichlorophenyl)methoxy]phenyl]ethenyl]-1H-imidazole, 1-methyl-5-nonyl-2-(phenylmethyl)-3-pyrrolidinol, 2',6'-dibromo-2-methyl-4'-trifluoromethoxy-4'-trifluoromethyl-1,3-thiazole-5-carboxanilide, 2,6-dichloro-5-(methylthio)-4-pyrimidinylthiocyanate, 2,6-dichloro-N-(4-trifluoromethylbenzyl)benzamide, 2,6-dichloro-N-[[4-(trifluoromethyl)phenyl]methyl]benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy-4-O-(4-O-methyl-β-D-glycopyranosyl)-α-D-glucopyranosyl]amino]-4-methoxy -1H-pyrrolo[2,3-d]pyrimidine-5-carbonitrile, 2-aminobutane, 2-bromo-2-(bromomethyl)pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)acetamide, 2-phenylphenol (OPP), 3,4-dichloro-1-[4-(difluoromethoxy)phenyl]-1H-pyrrole-2,5-dione, 3,5-dichloro-N-[cyano[(1-methyl-2-propynyl)oxy]methyl]benzamide, 3-(1,1-dimethylpropyl)-1-oxo-1H-indene-2-carbonitrile, 3-[2-(4-chlorophenyl)-5-ethoxy-3-isoxazolidinyl]pyridine, 4-chloro-2-cyano-N,N-dimethyl-5-(4-methylphenyl)-1H-imidazole-1-sulphonamide, 4-methyltetrazolo[1,5-a]quinazolin-5(4H)-one, 8-hydroxyquinoline sulphate, 9H-xanthene-2-[(phenylamino)carbonyl]-9-carboxylic hydrazide, bis(1-methylethyl)-3-methyl-4-[(3-methylbenzoyl)oxy]-2,5-thiophenedicarboxylate, cis-1-(4-chlorophenyl)-2-(1H-1,2,4-triazol-1-yl)cycloheptanol, cis-4-[3-[4-(1,1-dimethylpropyl)phenyl-2-methylpropyl]-2,6-dimethylmorpholine-hydrochloride, ethyl [(4-chlorophenyl)azo]cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,6-dimethylphenyl)-2-methoxy-N-(tetrahydro-2-oxo-3-furanyl)acetamide, N-(2,6-dimethylphenyl)-2-methoxy-N-(tetrahydro-2-oxo-3-thienyl)acetamide, N-(2-chloro-4-nitrophenyl)-4-methyl-3-nitrobenzenesulphonamide, N-(4-cyclohexylphenyl)-1,4,5,6-tetrahydro-2-pyrimidineamine, N-(4-hexylphenyl)-1,4,5,6-tetrahydro-2-pyrimidineamine, N-(5-chloro-2-methylphenyl)-2-methoxy-N-(2-oxo-3-oxazolidinyl)acetamide, N-(6-methoxy-3-pyridinyl)cyclopropanecarboxamide, N-[2,2,2-trichloro-1-[(chloroacetyl)amino]ethyl]benzamide, N-[3-chloro-4,5-bis(2-propinyloxy)phenyl]-N'-methoxymethanimidamide, N-formyl-N-hydroxy-DL-alaninesodium salt, O,O-diethyl [2-(dipropylamino)-2-oxoethyl]ethylphosphoramidothioate, O-methyl S-phenyl phenylpropylphosphoramidothioate, S-methyl 1,2,3-benzothiadiazole-7-carbothioate, spiro[2H]-1-benzopyrane-2,1'(3'H)-isobenzofuran]-3'-one,
4-[(3,4-dimethoxyphenyl)-3-(4-fluorophenyl)acryloyl]morpholine Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis,*baculoviruses, *Beauveria bassiana, Beauveria tenella,* bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaphorthrin, chromafenozide, cis-resmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, dicofol, diflubenzuron, dimethoat, dimethylvinphos; diofenolan, disulfoton, docusat-sodium, dofenapyn, eflusilanate, emamectin, empenthrin, endosulfan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb, granulosis viruses,
halofenozide, HCH, heptenophos, hexaflumuron, hexythiazox, hydroprene,
imidacloprid, indoxacarb, isazofos, isofenphos, isoxathion, ivermectin,
nuclear polyhedrosis viruses,
lambda-cyhalothrin, lufenuron,
malathion, mecarbam, metaldehyde, methamidophos, *Metharhizium anisopliae, Metharhizium flavoviride,* methidathion, methiocarb, methoprene, methomyl, methoxyfenozide, metolcarb, metoxadiazone, mevinphos, milbemectin, milbemycin, monocrotophos,
naled, nitenpyram, nithiazine, novaluron,
omethoate, oxamyl, oxydemethon M,
*Paecilomyces fumosoroseus,* parathion A, parathion M, permethrin, phenthoate, phorat, phosalone, phosmet, phosphamidon, phoxim, pirimicarb, pirimiphos A, piriniphos M, profenofos, promecarb, propargite, propoxur, prothiofos, prothoat, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, spirodiclofen, sulfotep, sulprofos, tau-fluvalinate, tebufenozide, tebufenpyrad, tebupirimiphos, teflubenzuron, tefluthrin, temephos, temivinphos, terbufos, tetrachlorvinphos, tetradifon, theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, *Verticillium lecanii,*
YI 5302
zeta-cypermethrin, zolaprofos
(1R-cis)-[5-(phenylmethyl)-3-furanyl]methyl 3-[(dihydro-2-oxo-3(2H)-furanylidene)methyl]-2,2-dimethylcyclopropanecarboxylate,
(3-phenoxyphenyl)methyl 2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydrooxazole,
2-(acetyloxy)-3-dodecyl-1,4-naphthalenedione,
2-chloro-N-[[[4-(1-phenylethoxy)phenyl]amino]carbonyl]-benzamide,
2-chloro-N-[[[4-(2,2-dichloro-1,1-difluoroethoxy)phenyl]amino]carbonyl]benzamide,
3-methylphenyl propylcarbamate,
4-[4-(4-ethoxyphenyl)-4-methylpentyl]-1-fluoro-2-phenoxybenzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)hydrazinobenzoic acid,
2,2-dimethyl-3-(2,4-dichlorophenyl)-2oxo-1-oxaspiro[4.5]dec-3-en4-yl butanoate,
[3-[(6-chloro-3-pyridinyl)methyl]-2-thiazolidinylidene]cyanamide,
dihydro-2-(nitromethylene)-2H-1,3-thiazine-3(4H)-carboxaldehyde,
ethyl [2-[[1,6-dihydro-6-oxo-1-(phenylmethyl)-4-pyridazinyl]oxy]ethyl]carbamate,
N-(3,4,4-trifluoro-1-oxo-3-butenyl)glycine,
N-(4-chlorophenyl)-3-[4-(difluoromethoxy)phenyl]4,5-dihydro-4-phenyl -1H-pyrazole-1-carboxamide,
N-[(2-chloro-5-thiazolyl)methyl]-N'-methyl-N"-nitroguanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl [2-(dipropylamino)-2-oxoethyl]ethylphosphoramidothioate,
N-cyanomethyl-4-trifluoromethylnicotinamide,
3,5-dichloro-1-(3,3-dichloro-2-propenyloxy)-4-[3-(5-trifluoromethylpyridin-2-yloxy)propoxy]benzene.

A mixture with other known active compounds, such as herbicides, or with fertilizers and growth regulators, is also possible.

In addition, the active compound according to the invention also has very good antimycotic activity. It has a very broad antimycotic activity spectrum in particular against dermatophytes and yeasts, moulds and diphasic fungi (for example *Candida* species such as *Candida albicans, Candida glabrata*) and also *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The list of these fungi by no means limits the mycotic spectrum covered, but is only for illustration.

The active compound can be used as such, in the form of its formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compound by the ultra-low volume method, or to inject the active compound preparation or the active compound itself into the soil. It is also possible to treat the seeds of the plants.

As already mentioned above, the active compound according to the invention can be used to treat all plants and parts thereof. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated. Plant cultivars are understood as meaning plants with novel properties ("traits") which have been grown by conventional cultivation, by mutagenesis or by recombinant DNA techniques. These may be cultivars, biotypes or genotypes.

Depending on the plant species or plant cultivars, their location and growth conditions (soils, climate, vegetation period, diet), the treatment may also result in superadditive ("synergistic") effects. Thus, for example, reduced application rates and/or a widening of the activity spectrum and/or an increase in the activity of the substance to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated include all plants which, in the genetic modification, received genetic material which imparts particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits which are also particularly emphasized are the increased resistance of plants to fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars having these genetic traits or genetic traits still to be developed, which cultivars will be developed and/or marketed in the future.

The plants listed can be treated in a particularly advantageous manner with the active compound according to the invention or its mixtures.

The preparation of crystal form II of the triazole derivative of the formula (A) is illustrated by the examples below.

PREPARATION EXAMPLES

Example 1

5 g of the triazole derivative of the formula (A) in crystal form I are suspended in 50 g of methanol. The suspension is, with stirring, heated at 60° C. until the crystals of form I are completely dissolved. The mixture is then cooled to room temperature. This results in the precipitation of a crystalline product which is filtered off and dried at temperatures below 60° C. This gives 4 g of triazole derivative of the formula (A) in crystal form II. In the Raman spectrum, the product shows peak maxima at the wave numbers given in Table 1.

Melting point: 140.0° C. (peak maximum)

Example 2

5 g of the triazole derivative of the formula (A) in crystal form I are suspended in 40 g of acetone. The suspension is, with stirring, heated at 50° C. until the crystals of form I are completely dissolved. The mixture is then cooled to room temperature. This results in the precipitation of a crystalline product which is filtered off and dried at temperatures below 60° C. This gives 3 g of triazole derivative of the formula (A) in crystal form II. In the Raman spectrum, the product shows peak maxima at the wave numbers given in Table 1.

Melting point: 138.6° C. (peak maximum)

Example 3

5 g of the triazole derivative of the formula (A) in crystal form I are suspended in 40 g of ethyl acetate. The suspension is, with stirring, heated at 70° C. until the crystals of form I are completely dissolved. The mixture is then cooled to room temperature. This results in the precipitation of a crystalline product which is filtered off and dried at temperatures below 60° C. This gives 3 g of triazole derivative of the formula (A) in crystal form II. In the Raman spectrum, the product shows peak maxima at the wave numbers given in Table 1.

Melting point: 138.7° C. (peak maximum)

Example 4

5 g of the triazole derivative of the formula (A) in crystal form I are suspended in 100 g of distilled water. The suspension is stirred at 80° C. for 2 weeks. The resulting crystalline product is then filtered off and dried at temperatures below 60° C. This gives 4 g of triazole derivative of the formula (A) in crystal form II. In the Raman spectrum, the product shows peak maxima at the wave numbers given in Table 1.

Melting point: 138.4° C. (peak maximum)

Comparative Example A

At −20° C., 8.4 ml (21 mmol) of n-butyllithium in hexane are added to a mixture of 3.12 g (10 mmol) of 2-(1-chlorocyclopropyl)-1-(2-chlorophenyl)-3-(1,2,4-triazol-1-yl)propan-2-ol and 45 ml of absolute tetrahydtofuran, and the mixture is stirred at 0° C. for 30 minutes. The reaction mixture is then cooled to −70° C., 0.32 g (10 mmol) of sulphur powder is added and the mixture is stirred at −70° C. for 30 minutes. The mixture is warmed to −10° C., ice-water is added and the pH of the mixture is adjusted to 5 by addition of dilute sulphuric acid. The mixture is extracted repeatedly with ethyl acetate and the combined organic phases are dried over sodium sulphate and concentrated under reduced pressure. This gives 3.2 g (93% of theory) of 2-(1-chlorocyclopropyl)-1-(2-chlorophenyl)-3-(5-mercapto-1,2,4-triazol-1-yl)-propan-2-ol in crystal form I. In the Raman spectrum, the product shows peak maxima at the wave numbers given in Table 4.

Melting point: 139.3° C.

What is claimed is:

1. Crystal form II of 2-[2-(1-chlorocyclopropyl)-3-(2-chlorophenyl)-2-hydroxypropyl]-2,4-dihydro-3H-1,2,4-triazole-3-thione of the formula

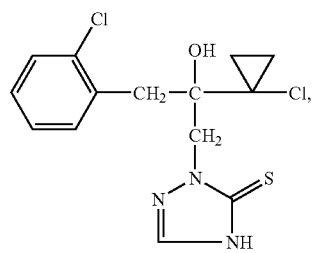

(A)

characterized by
(a) peak maxima in the Raman spectrum at the following wave numbers in cm$^{-1}$

| |
|---|
| 3220 |
| 3151 |
| 3063 |
| 3016 |
| 2927 |
| 1542 |
| 1476 |
| 1455 |
| 1445 |
| 1424 |
| 1407 |
| 1375 |
| 1351 |
| 1339 |
| 1324 |
| 1290 |
| 1220 |
| 1204 |
| 1184 |
| 1169 |
| 1137 |
| 1123 |
| 1101 |
| 1065 |
| 1052 |
| 1038 |
| 1032 |
| 1001 |
| 963 |
| 954 |
| 922 |
| 912 |
| 889 |
| 876 |
| 869 |
| 849 |
| 822 |
| 796 |
| 782 |
| 759 |
| 752 |
| 748 |
| 725 |
| 680 |

(b) the following bond lengths in Å and bond angles in °

| Bond | Length [Å] | Bonds | Angle [°] |
|---|---|---|---|
| N(1)-C(5) | 1.350 (3) | C(5)-N(1)-N(2) | 112.8 (2) |
| N(1)-C(6) | 1.454 (3) | N(2)-N(1)-C(6) | 120.6 (2) |

-continued

| Bond | Length [Å] | Bonds | Angle [°] |
|---|---|---|---|
| C(3)-N(4) | 1.360 (3) | N(2)-C(3)-N(4) | 111.9 (2) |
| S(5)-C(5) | 1.689 (2) | N(1)-C(5)-N(4) | 103.6 (2) |
| O(7)-C(7) | 1.433 (3) | N(4)-C(5)-S(5) | 127.8 (2) |
| C(7)-C(8) | 1.539 (3) | O(7)-C(7)-C(6) | 104.8 (2) |
| C(9)-C(14) | 1.393 (4) | C(6)-C(7)-C(15) | 113.6 (2) |
| Cl(10)-C(10) | 1.743 (3) | C(6)-C(7)-C(8) | 109.9 (2) |
| C(11)-C(12) | 1.384 (4) | C(9)-C(8)-C(7) | 117.2 (2) |
| C(13)-C(14) | 1.391 (4) | C(14)-C(9)-C(8) | 119.6 (2) |
| C(15)-C(16) | 1.490 (4) | C(11)-C(10)-C(9) | 122.4 (2) |
| C(16)-C(17) | 1.521 (4) | C(9)-C(10)-Cl(10) | 120.1 (3) |
| N(1)-N(2) | 1.377 (3) | C(13)-C(12)-C(11) | 119.9 (3) |
| N(2)-C(3) | 1.301 (4) | C(13)-C(14)-C(9) | 121.9 (3) |
| N(4)-C(5) | 1.361 (3) | C(16)-C(15)-C(7) | 123.2 (2) |
| C(6)-C(7) | 1.533 (3) | C(16)-C(15)-Cl(15) | 115.7 (2) |
| C(7)-C(15) | 1.536 (3) | C(7)-C(15)-Cl(15) | 112.2 (2) |
| C(8)-C(9) | 1.515 (3) | C(15)-C(17)-C(16) | 59.0 (2) |
| C(9)-C(10) | 1.395 (4) | C(5)-N(1)-C(6) | 126.6 (2) |
| C(10)-C(11) | 1.382 (4) | C(3)-N(2)-N(1) | 103.5 (2) |
| C(12)-C(13) | 1.379 (5) | C(3)-N(4)-C(5) | 108.2 (2) |
| Cl(15)-C(15) | 1.773 (3) | N(1)-C(5)-S(5) | 128.5 (2) |
| C(15)-C(17) | 1.503 (4) | N(1)-C(6)-C(7) | 113.3 (2) |
| | | O(7)-C(7)-C(15) | 108.9 (2) |
| | | O(7)-C(7)-C(8) | 111.7 (2) |
| | | C(15)-C(7)-C(8) | 108.1 (2) |
| | | C(14)-C(9)-C(10) | 116.5 (2) |
| | | C(10)-C(9)-C(8) | 123.9 (2) |
| | | C(11)-C(10)-Cl(10) | 117.4 (2) |
| | | C(10)-C(11)-C(12) | 119.5 (3) |
| | | C(12)-C(13)-C(14) | 119.8 (3) |
| | | C(16)-C(15)-C(17) | 61.1 (2) |
| | | C(17)-C(15)-C(7) | 120.6 (2) |
| | | C(17)-C(15)-Cl(15) | 115.1 (2) |
| | | C(15)-C(16)-C(17) | 59.9 (2) |

(c) a unit cell having the following dimensions

| | |
|---|---|
| a = 9.8927(8) Å | α = 90° |
| b = 9.5635 (8) Å | β = 92.651 (6)° |
| c = 16.4448 (10) Å | γ = 90° |

(d) a melting point of 138.3° C.

and (e) a particle density of 1.471 Mg/m$^3$.

2. A process for preparing crystal form II of the triazole derivative of the formula (A) according to claim 1 comprising treating crystal form I of the triazole derivative of the formula (A) at temperatures between 0° C. and 90° C. in the presence of (i) water and/or (ii) one or more aliphatic alcohols having 1 to 10 carbon atoms and/or (iii) one or more dialkyl ketones having 1 to 4 carbon atoms in each alkyl moiety and/or (iv) one or more alkyl alkylcarboxylates having 1 to 4 carbon atoms in each alkyl moiety.

3. A microbicidal composition comprising a triazole derivative of the formula (A) according to claim 1 in the crystal form II and one or more extenders and/or surfactants wherein the triazole derivative is present in the form of powders, pastes, dusts and granules.

4. A method for controlling unwanted microorganisms comprising applying an effective amount of crystal form II of the triazole derivative of the formula (A) according to claim 1 to the microorganisms and/or their habitat.

5. A process for preparing microbicidal compositions comprising mixing crystal form II of the triazole derivative of the formula (A) according to claim 1 with one or more extenders and/or surfactants wherein the triazole derivative of the resultant composition is in the form of powders, pastes, dusts and granules.

* * * * *